United States Patent [19]

Neville et al.

[11] 3,978,987

[45] Sept. 7, 1976

[54] CUTTING OF A STREAM OF TOBACCO INTO MEASURED WEIGHT PORTIONS

[75] Inventors: Richard Ernest Gartside Neville, Salisbury; Frank Baxter Bardsley, Newton Toney, both of England

[73] Assignee: AMF Incorporated, White Plains, N.Y.

[22] Filed: June 18, 1974

[21] Appl. No.: 480,453

[30] Foreign Application Priority Data

July 3, 1973 United Kingdom............... 31664/73

[52] U.S. Cl.................................. 209/121; 177/50; 222/52
[51] Int. Cl.²........................................... B07C 5/16
[58] Field of Search................ 209/121; 250/223 R; 177/16, 50, DIG. 6, 119, 120; 222/52, 56, 77

[56] References Cited
UNITED STATES PATENTS

| | | | |
|---|---|---|---|
| 2,965,050 | 12/1960 | Doering | 177/16 X |
| 3,095,091 | 6/1963 | Blunt | 209/121 |
| 3,278,747 | 10/1966 | Ohmart | 177/16 |
| 3,561,552 | 2/1971 | Rischke | 222/56 X |
| 3,578,094 | 5/1971 | Henry et al. | 177/119 X |
| 3,823,821 | 7/1974 | Wallace | 209/121 |

Primary Examiner—Robert B. Reeves
Assistant Examiner—Joseph J. Rolla
Attorney, Agent, or Firm—George W. Price; Charles J. Worth

[57] ABSTRACT

Method and apparatus for dispensing particulate material in portions of predetermined weight by providing a flow of material measurable by a radiation detector, measuring the flow rate per unit time of the material and removing successive determined portions of the material from the flow when the measurement indicates that each such portion is of predetermined desired weight.

25 Claims, 9 Drawing Figures

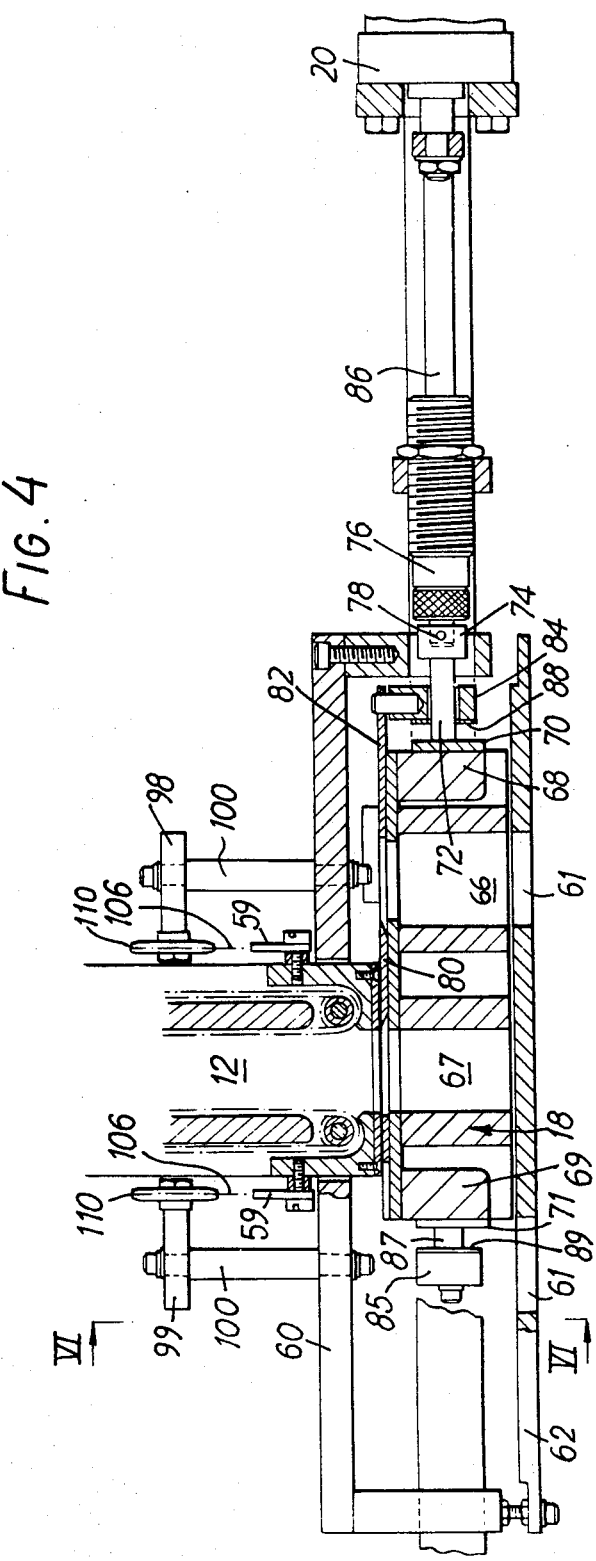

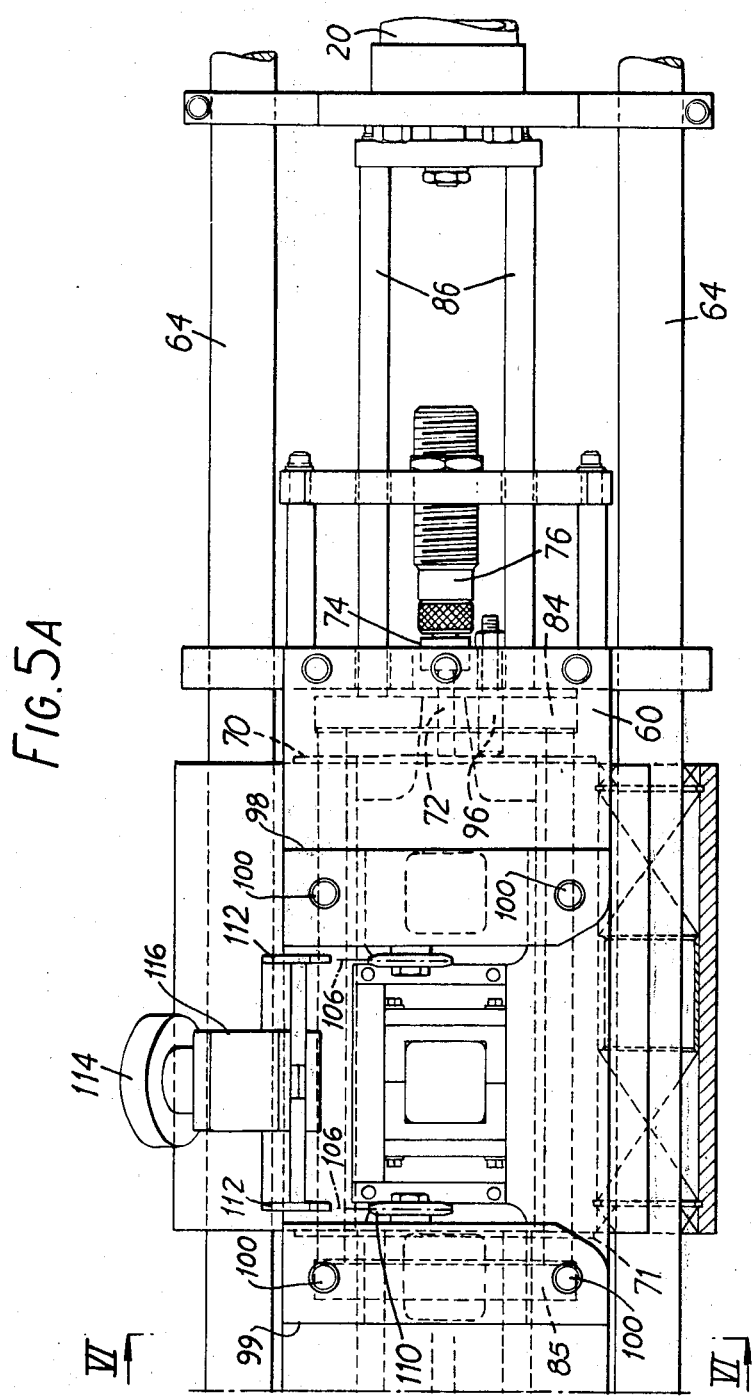

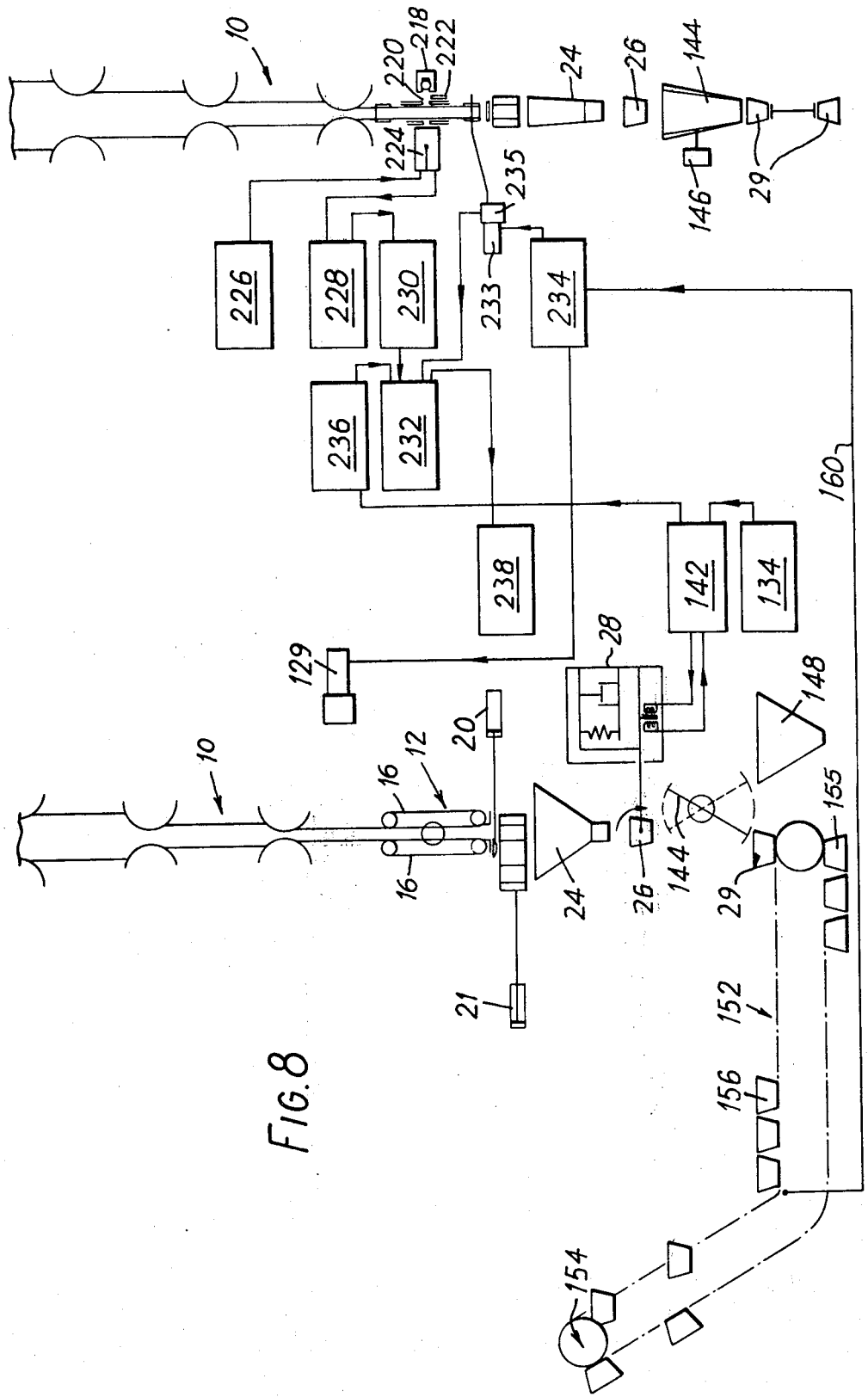

CUTTING OF A STREAM OF TOBACCO INTO MEASURED WEIGHT PORTIONS

This invention relates generally to a machine for automatically dispensing small constant weight portions of particulate material, especially of fine-cut long-stranded hand rolling or pipe tobacco for subsequent packing, and more particularly to means for gauging a stream of tobacco and operating a cut-off to produce accurate weight portions without the need for add-back.

In known methods an initial portion of tobacco is dispensed, the weight of which is below the desired weight, and then fines are added to make-up the weight. The need to add make-up material reflects the difficulty of dispensing the correct weight initially with such long stranded and matted material.

Hand rolling tobacco used for "roll your own" cigarettes consists of fine shreds cut from tobacco leaf, typically at approximately 100 cuts per inch compared with approximately 50 cuts per inch or less for machine manufactured cigarettes. The moisture content of the tobacco is typically 26% compared with 13% for manufactured cigarettes, and stripped leaf rather than threshed leaf is used so that the shreds or strands are considerably longer than for manufactured cigarettes. Stripped leaf has had the stem or mid-rib of the leaf removed by hand or machine in such a way that the lamina of the leaf is still in one piece, whereas threshed leaf has had the stem removed by successive stages of threshing so that the lamina is reduced to small pieces.

The fine cut and strand length combine to give a more cohesive and tangled or matted bulk than cigarette tobacco for machine manufacture. The higher moisture content reduces breakage or degradation of the strands and results in a higher bulk density typically 10 to 12 lb/ft$^3$ as compared with 6 to 8 lb/ft$^3$ for manufactured cigarette tobacco, and also reduces the resilience of the bulk so that the recovery of volume after compression is less than for manufactured cigarette tobacco.

The initial portion of tobacco is dispensed by methods depending on volume, pressure or weight.

In one method a constant volume is dispensed by first producing an approximately uniform stream of tobacco and then cutting the stream at regular intervals or filling a constant volume and then parting or cutting the stream. The segregated or measured portion of the stream is then weighed and make-up material is added to correct the weight error. In a refinement of this method a constant volume device is filled by the stream of tobacco to a fixed pressure and the stream then cut.

In the above methods the weight of the initial portion is based on volume or volume plus pressure. Due to the variation in bulk density of fine and long strand cut tobacco which, in the form required, is between 10 and 16 lb/ft$^3$ compared with a solid density of 40 lb/ft$^3$, the initial weight is not very accurate so a make-up of "fines" has to be added. The fines are short strands of tobacco which are separated from the main bulk or separately produced by carding drums and are in a comminuted form in which they can be metered out in very small amounts.

In another method the initial portions of tobacco are dispensed by feeding a small cross-section stream of material onto a weighing conveyor or pan and parting or cutting the stream when the desired under weight on the conveyor or pan has been achieved. In this method, the difficulty is to produce a fine enough stream and a short enough weighing conveyor to give sufficient resolving power to make the weighing conveyor sensitive to the variations of flow and hence to decide accurately when to part the stream.

The use of add-back is undesirable because it involves deliberate degradation of the hand rolling tobacco, the hall mark of which is its long strand length. The fines used for add-back are inevitably end up at the surface of the portion of tobacco and tend to be conspicuous when a customer opens a packet.

An object of the present invention is to dispense an accurate weight portion of cut tobacco initially in one step without the need for subsequent add-back of fines.

Another object of the invention is to provide a method for dispensing particulate material in portions of predetermined weight, comprising feeding particulate material through a measuring region, producing a signal representative of the flow rate of said particulate material through the measuring region by means of a radiation source and detector, integrating the flow rate signal with respect to time to give a value proportional to the total weight of the particulate material which has been fed through the measuring region, and initiating separation of the particulate material which has been fed through the measuring region from the remainder of said particulate material, particularly tobacco, when said integrated value reaches a value corresponding to the predetermined desired weight.

And another object of the invention is to provide apparatus, comprising means for feeding particulate material through a measuring region, a source of radiation and a radiation detector positioned adjacent and on opposite sides of the measuring region for producing a signal representative of the flow rate of the particulate material passing through the measuring region, means for integrating the signal with respect to time to give a value proportional to the total weight of particulate material which has been fed through the measuring region, means for separating the particulate material which has been fed through the measuring region from the remainder thereof, and means for initiating the separation when the integrated value corresponds to the predetermined desired weight.

A measuring tube having moving walls for feeding particulate material, and a radiation source and detector positioned along a part of the tube may be used; the tube in the vicinity of the radiation source and detector constituting the measuring region. Ideally, radiation from the radiation source passes through a window in the tube, through particulate material in the tube and out of the tube via another window to be detected by the radiation detector. The logarithm of the signal from the radiation detector is inversely proportional to flow rate and may be amplified and corrected by a linearizing and inverting circuit to provide the desired proportional signal. The corrected signal when integrated is then proportional to the weight per unit area of material in the measuring region, and this can be multiplied by a signal proportional to the speed of the material through the measuring region where this is known to give a signal which is proportional to the total weight of material which has been fed through the measuring region.

The particulate material is preferably separated by cutting with a knife, and after cutting, the separated portions of material are weighed and rejected if not of the predetermined desired weight.

The foregoing and other objects and advantages of the invention will appear more fully hereinafter from a consideration of the detailed description which follows, taken together with the accompanying drawings wherein several embodiments of the invention are illustrated by way of example. It is to be expressly understood, however, that the drawings are for illustration purposes only and are not to be construed as defining the limits of the invention.

FIG. 1 diagrammatically illustrates apparatus made in accordance with the invention.

FIG. 4 is an elevational view partly in section to better illustrate the horizontally movable carriage assembly of the apparatus of FIG. 1.

Figure 5B:
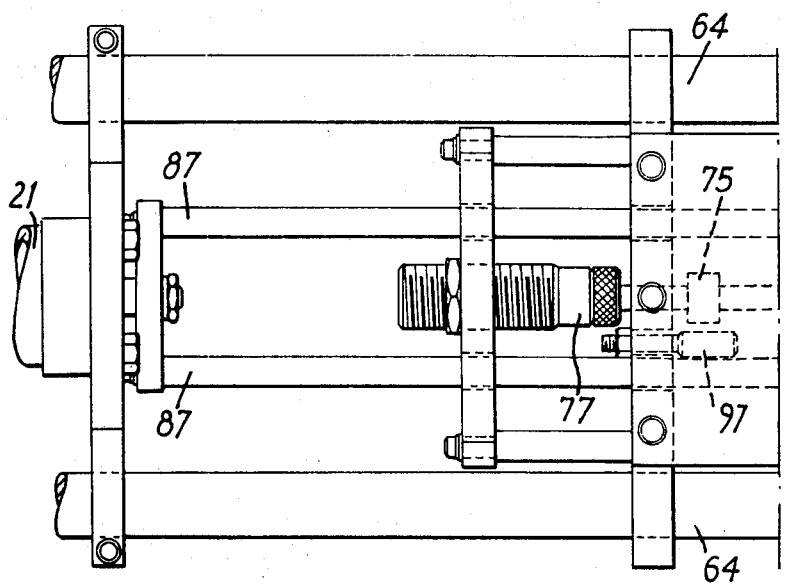

FIGS. 5A and 5B together form an enlarged plan view of the carriage assembly of FIG. 4.

Figure 6:
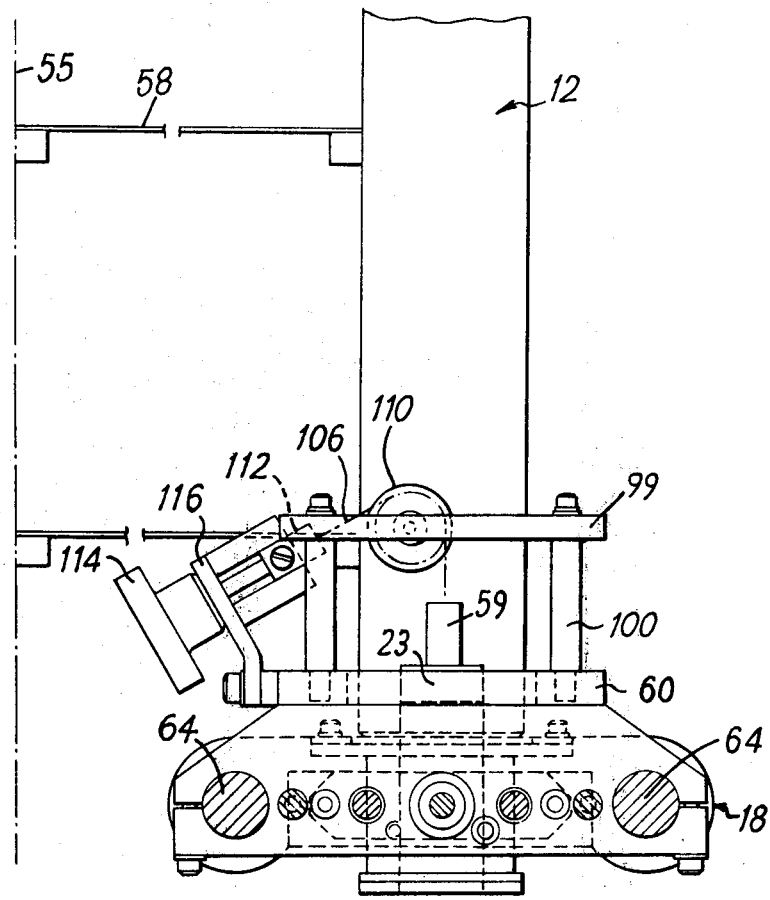

FIG. 6 is a sectional view taken on the line VI—VI of FIGS. 4 and 5A.

Figure 7:
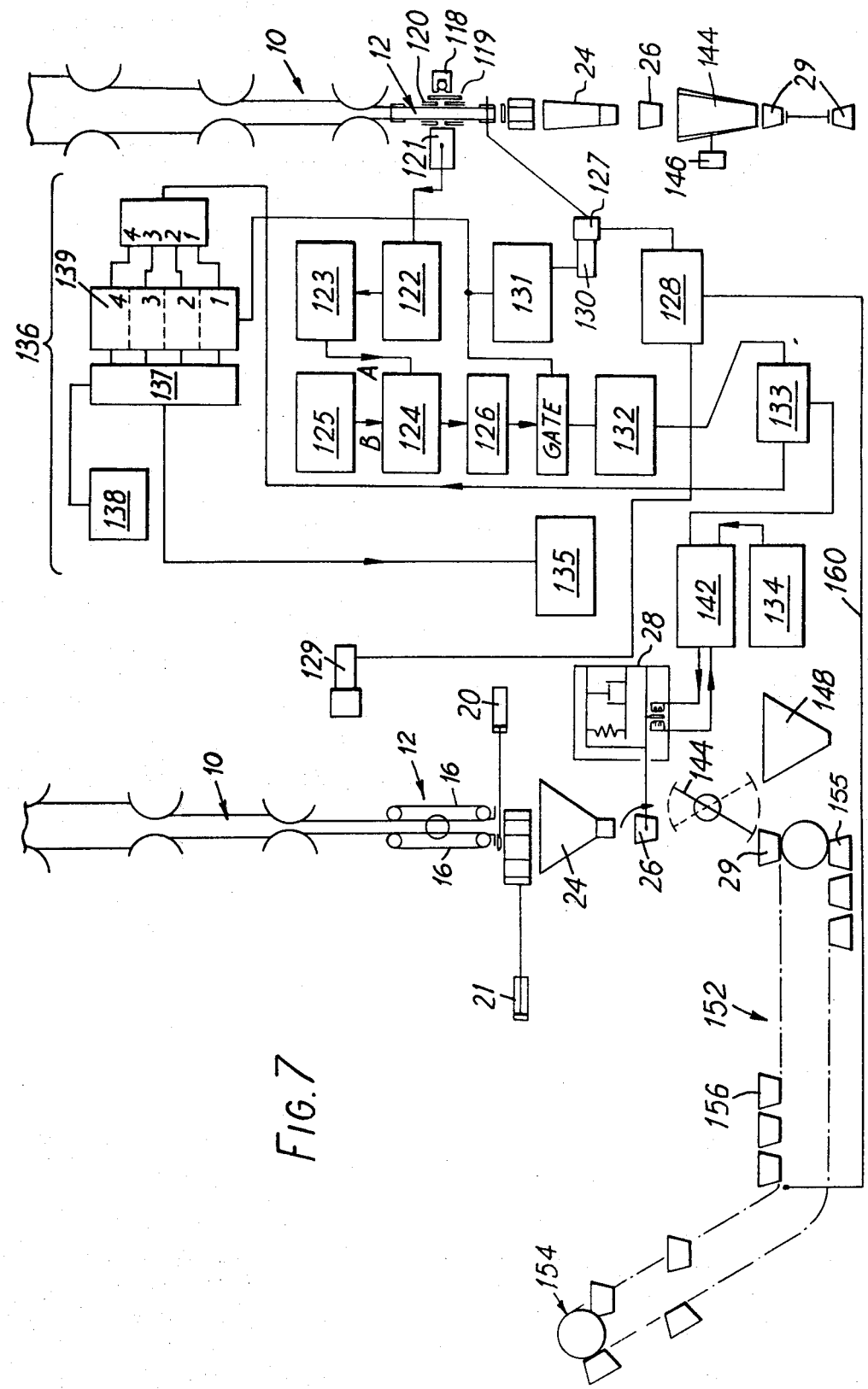

FIG. 7 diagrammatically illustrates digital circuitry for use with the apparatus (shown in front and side elevation) of FIGS. 1 to 6.

FIG. 8 diagrammatically illustrates analog circuitry for use with the apparatus (shown in front and side elevation) of FIGS. 1 to 6.

The stream of tobacco can be produced by various known means such as the feed units described in our U.S. Pat. application 420,126, filed Nov. 29, 1973, now U.S. Pat. No. 3,908,817, which shows, describes and claims a feeding device for the formation of a particularly small cross-section stream of tobacco with the minimum of degradation of the strand length. Such a feed unit 10 is diagrammatically shown in FIG. 1. The stream is then conveyed through a vertical axis rectangular cross-section conveyor gauging or measuring tube 12 comprising two opposed fixed walls and two opposed movable walls, the movable walls being formed by moving toothed belts 16 which convey the tobacco stream through the tube 12 at a known speed.

A horizontally movable carriage 18 is disposed below the measuring tube 12 and is provided with a double edged knife 80 (see FIG. 4) for cutting the stream of tobacco. The knife 80 and carriage 18 can be reciprocated by means of air cylinders 20 and 21 respectively. Cut tobacco falls from the carriage 18 through a chute 24 and into a pan 26 of a check weigher 28. After weighing, the cut portion of tobacco is discharged into one of a number of trucks 29 for transfer to a packing machine (not shown).

Carriage and knife solenoid valves 30 and 31 are mounted on respective air cylinders 20 and 21, and air reservoirs 32 and 33 are mounted in close proximity to the respective valves 30 and 31 to give the fastest possible carriage and knife reciprocation or operating speed.

Figure 1:
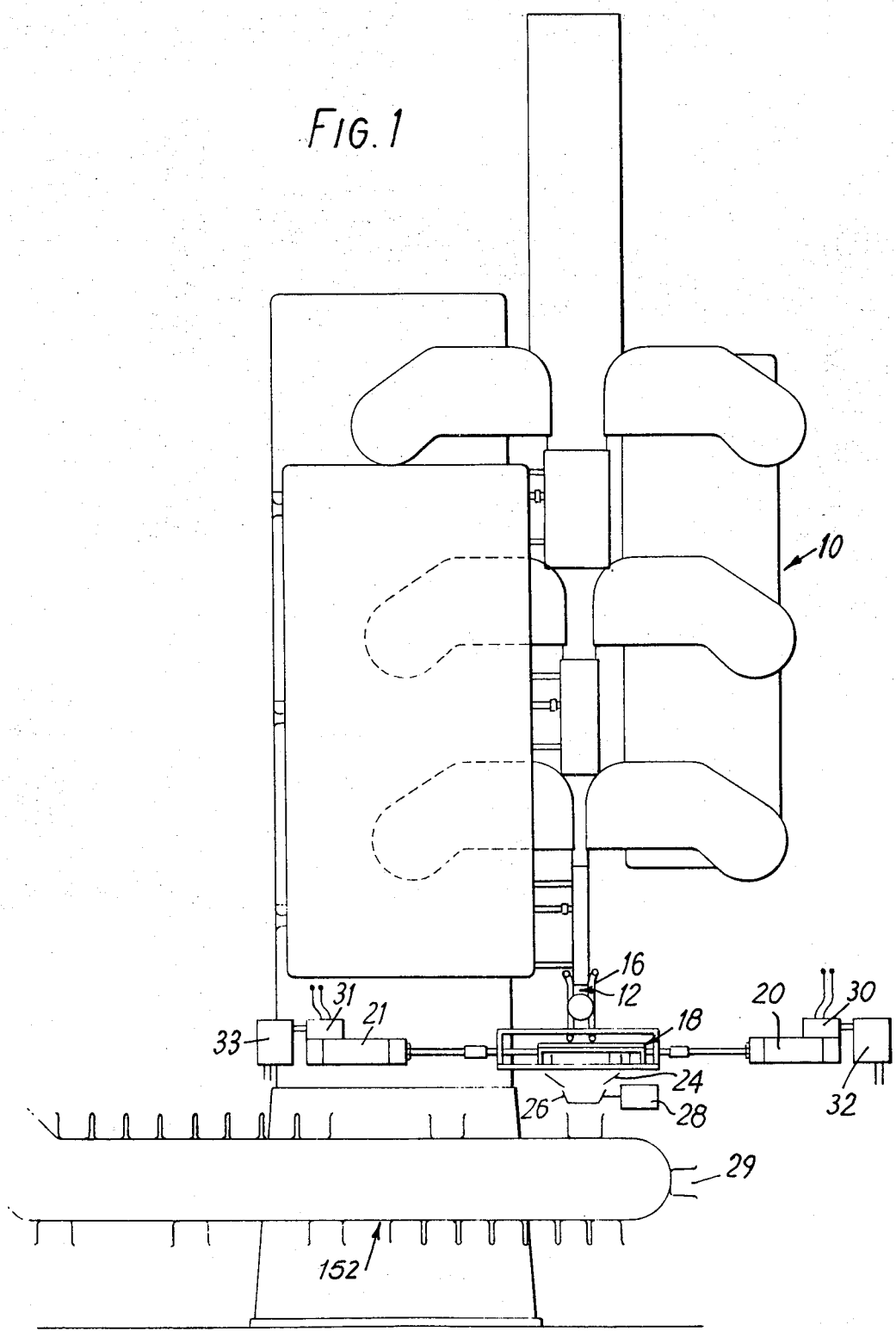
Figure 2:
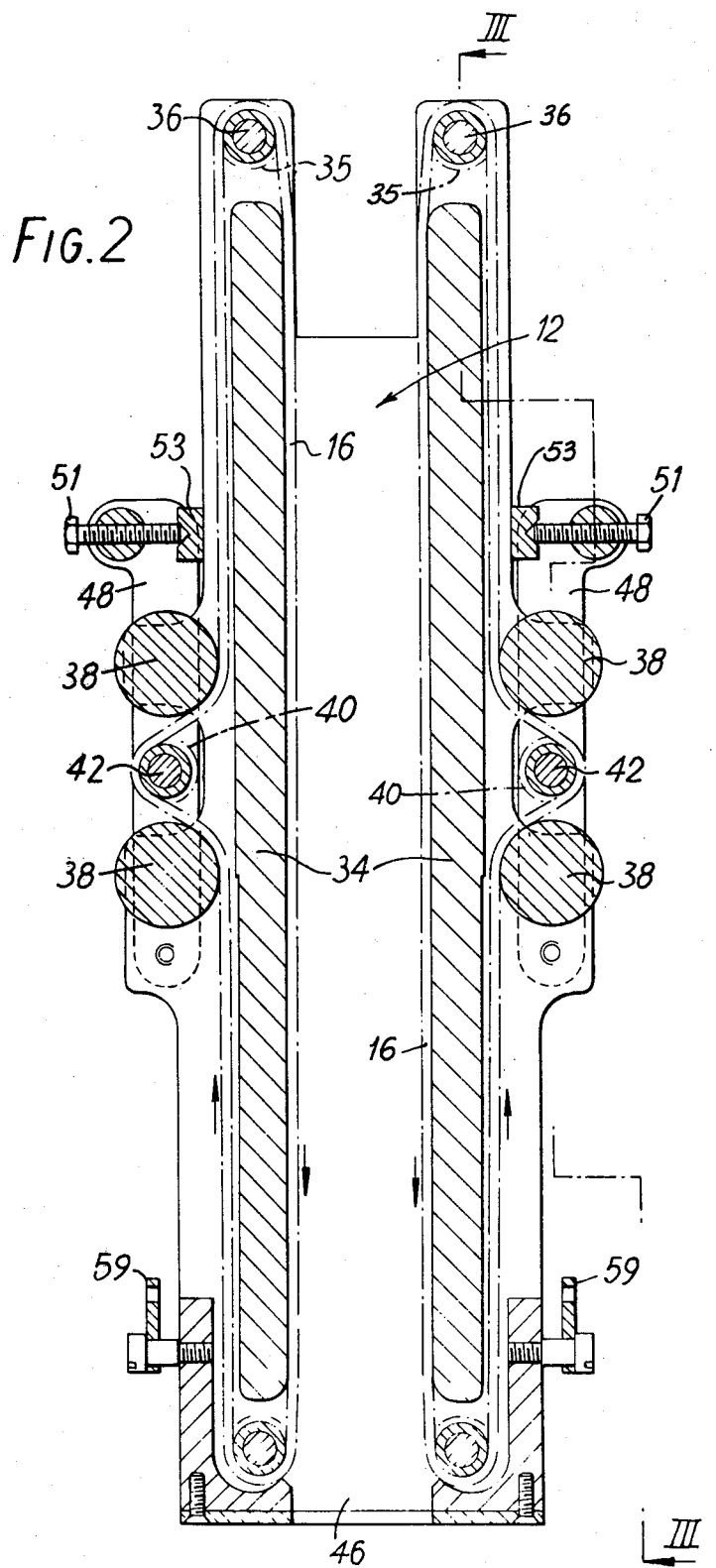
FIG. 2 is an enlarged sectional view of the measuring tube of the novel apparatus looking in the same direction as in FIG. 1 and disposed in the plane indicated by line II—II of FIG. 3.
Figure 3:
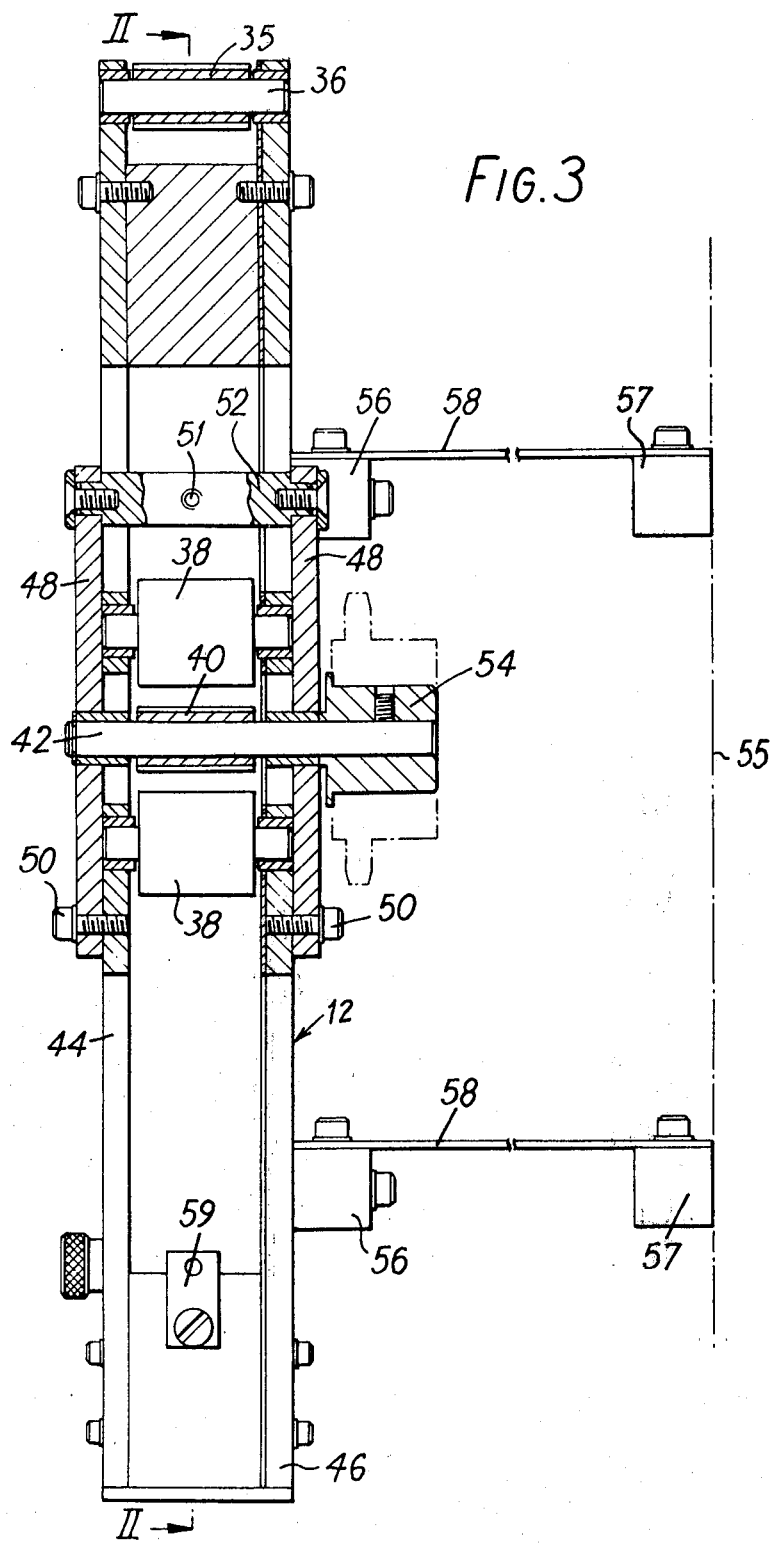
FIG. 3 is a sectional view of the measuring tube taken on the line III—III of FIG. 2.

FIGS. 2 and 3 show in more detail the measuring tube 12. Each of two opposite movable sides of the tube 12 comprises a belt guide 34 encircled by a toothed belt 16. At each end of each belt guide 34 and spaced therefrom are toothed wheels 35 carried on idler shafts 36 to support the belt 16. On the side of the belt guide 34 remote from the measuring tube interior, the belt 16 engages a pair of jockey wheels 38 and a toothed wheel 40 carried on a drive shaft 42. Each jockey wheel 38 is mounted in bearings on the fixed opposite walls or front and back plates 44 and 46, respectively. Each drive shaft 42 is rotatably mounted in a pair of spaced arms 48 pivoted at one end to the front and back plates 44 and 46 by a pin 50 and adjustable at the other end by an adjusting bolt 51 which is threaded into a cross rod 52 connected to both arms 48. The end of each bolt 51 abuts an adjusting bar 53 and adjustment of a bolt 51 tightens or loosens the operatively associated toothed belt 16, as desired. Secured to one end of each drive shaft 42 is a sprocket or chain wheel boss 54, the two chain wheel bosses being interconnected by a chain (not shown).

For the sake of clarity, the radiation equipment and the window and shield means to be described below are not shown in FIGS. 2 and 3. The measuring tube 12 is secured to a fixed support 55 by support blocks 56 and 57 connected respectively to the back plate 46 and to the fixed support 55 and to each other by spring steel support plates 58, as shown in FIG. 3. Chain anchors 59 are provided toward the lower end of the measuring tube 12 and will be further discussed below.

Referring now to FIGS. 4, 5A, 5B and 6, the horizontally movable or slidable carriage 18 is supported between upper and lower plates 60 and 62 fixed to a pair of parallel support bars 64 below the measuring tube 12. The carriage 18 has two chambers 66 and 67, and end plates 68 and 69 each fitted with a strike plate 70 and 71 respectively. Coming into contact with or engaging the strike plate 70 is a rod 72 which is connected by a pin 78 to a sleeve 74 of a shock absorber 76. The lower plate 62 has two spaced apertures 61 therein.

Between the horizontally slidable carriage 18 and the measuring tube 12 is the double edged knife 80 carried on a horizontally slidable frame 82 having knife drive end plates 84 and 85 at opposite ends and spaced further apart than the carriage end plates 68 and 69. The air cylinder 20 has a piston (not shown) the rod of which is connected to one end of each of a pair of drive rods 86. The other end of each of the rods 86 is secured to the knife drive end plate 84. The air cylinder 21 has a piston (not shown) the rod of which is connected to the carriage end plate 69 by a pair of drive rods 87. The surface of each knife drive end plate 84 and 85 facing the respective carriage end plates 68 and 69 are provided with cushions 88 and 89, respectively. Stops 96 and 97 are provided to limit the movement of the carriage 18.

A pair of pillars or spacer bolts 100 are provided to mount each of the brackets 98 and 99 in spaced relationship on the plate 60. The metering tube 12 extends between brackets 98 and 99, and through the plate 60; its lower end resting on top of the knife 80. The steel spring support plates 58 also locate the tube 12 against sideways loads which arise during cutting of the tobacco, and spring load the conveyor tube 12 against the knife 80. By suitable adjustment of the spring plate mountings 58 the pressure between the conveyor tube 12 and the knife 80 can be adjusted to give the most suitable cutting pressure. A suitable chain or cable 106 is connected to each chain anchor 59 on the conveyor tube 12 and passes over a sprocket wheel or pulley 110 supported on each of the brackets 98 and 99; the other end of each chain or cable 106 being secured to a second chain anchor 112 attached to the shaft of a hand wheel 114. The hand wheel shaft passes through a bracket 116 attached to the plate 60 so that by turning the hand wheel 114, the measuring tube 12 may be lifted about ½ inch. This enables the operator to remove the knife 80 for sharpening or replace the knife by a previously sharpened spare knife.

Referring to FIG. 7, an X-ray tube 118 is mounted in a shield (not shown) opposite the back plate 46 of the measuring tube 12 and is provided with a microswitch interlock (not shown) as a safety device to prevent the X-ray tube from being operated when the shield is not in position. The radiation from the X-ray tube 118 passed through a collimator 119 and a window 120 into the tobacco flow in the measuring tube 12. A radiation detector 121 in the form of a scintillation counter is mounted opposite the front plate 44 of the measuring tube 12 and pulses from this counter in response to detected radiation are fed to a prescaling unit 122. The output of the prescaling unit 122 is fed to a log rate meter 123, whose analogue output A is proportional to the logarithm of its input. A summer 124 adds together the signal A and a standard radiation count B generated as a preset D.C. signal in unit 125. The analogue output of the summer 124 is passed to an analogue-to-digital converter 126.

The moving belt 16 of the measuring tube 12 is driven by a variable speed motor 127, which also drives the feed unit 10. A digital transducer 130 is linked to the motor 127 and produces a pulse for each fixed movement of the belt, and this pulse is fed to a constant pulse width unit 131. In this application each pulse from the digital transducer 130 corresponds to a belt length of 0.002 inches.

The pulses from the digital transducer 130 operate a gate positioned between the analogue-to-digital converter 126 and a counter 132, so that the pulses from the converter 126 are counted only when the gate is open. The result of the pulse count is electronically compared by a comparator 133 against a reference from manually preset unit 134 which corresponds to the desired tobacco weight.

The comparator 133 provides an output signal when the input from the counter 132 is equal to or is greater than the manually set reference. The comparator pulse is used to reset the counter 132 and to trigger a control unit 135 for movement of the knife 80 and carriage 18. However, between the comparator 133 and the control unit 135 a displacement unit 136 is provided which is necessary to take account of the distance travelled by the tobacco from the measuring window to the knife for cutting the tobacco. The distance or length of belt travel is set on a comparator 137 by a unit 138. The distance between measurement and cutting is such that up to four cut pulses must be stored. The displacement unit 136 comprises four counters 139 which count belt pulses from the constant pulse width unit 133. The contents of the four counters 139 are compared against the preset distance by comparator 137 and the first counter to equal the preset distance results in activation of the knife and carriage control unit 135. At the same time, the appropriate counter 139 is reset and does not count again until actuated by a measurement pulse from comparator 133.

Below the chamber 66 or 67 of the carriage 18 there is the chute 24 through which the tobacco falls into the check weigher pan 26. The desired weight is preset on the unit 134 which controls the output of an oscillator-amplifier 142 to the check weigher 28. Cut portions of tobacco which are of the correct desired weight are deflected by a chute or deflector plate 144 into one of a number of trucks 29, while portions which are under or over weight cause the chute plate 144 to be rotated by a rotary solonoid 146 which deflects the portion into a reject hopper 148. At the end 154 of the conveyor 152 on which the trucks 29 are mounted, the portions of tobacco of correct weight are discharged from the trucks 29 into a tobacco packer (not shown).

Referring to FIG. 8, a radioisotope source 218 of beta or gamma radiation is mounted opposite the back plate 46 of the measuring tube conveyor 12 and is contained in a shield (not shown) with a window 220 to permit radiation to pass through the tobacco stream; the window 220 having a safety shutter 222 which can be closed when radiation is not required. A radiation detector 224, in the form of an ionization chamber, is mounted opposite the front plate 44 and is arranged to collect all the radiation passing through the tobacco stream. The ionization chamber 224 is connected to a power supply 226, and to a detector amplifier 228 providing an output which passes through a linearizer-inverter 230 to a flow integrator 232. The moving belt 16 of the measuring tube 12 is driven by a variable speed motor 233 which is regulated by a control unit 234. A tachometer 235 connected to the moving belt provides a signal proportional to the belt speed, and this signal is fed to the flow integrator 232 where it is multiplied by the linearized and inverted analogue signal from the ionization chamber 224. Also fed to the flow integrator 232 is a preset signal from unit 236 indicative of the desired total flow of tobacco. Controls 238 governing the movement of the knife 80 and carriage 18 are triggered from the flow integrator 232.

The operation of the apparatus shown in FIGS. 4 to 6 is as follows:

The compartment 67 of the carriage 18 forms an enlarged extension of the measuring tube cross-section, is positioned below the measuring tube 12 and tobacco fed into it from the measuring tube 12.

Upon the receipt of a pulse from the control unit 135 or 238, compressed air is fed to the cylinders 20 and 21 causing the drive rods 86 and the knife drive end plate 84 to start moving to the left in FIG. 4. Because of the higher inertia of the carriage 18 compared with the knife 80 and its frame 82, for a finite period of time the knife 80 moves while the carriage 18 remains stationary. The knife 80 thus begins to travel across the top of the chamber 67 cutting the tobacco in the process. Eventually the cushion 88 on the knife drive end plate 84 abuts the strike plate 70 which causes the carriage to move to the left. At the same time, the inertia of the carriage 18 is overcome and the drive rods 87 are driven to the left in FIG. 4 taking the carriage 18 with them. For efficient cutting of the tobacco, it is essential that the knife 80 precedes the carriage 18 in this manner. This movement of the carriage 18 and knife 80 together continues until a stop in the cylinder 20 causes the knife drive plate 84 to stop and all the tobacco in the chamber 67 has been cut from the supply or flow in the measuring tube 12 by the knife 80. The carriage 18 continues to move alone, until the carriage end plate 69 strikes the stop 97 and, in this position, as the chamber 66 is being filled with tobacco from the measuring tube 12, tobacco in chamber 67 falls through one of the apertures 61 into the chute 24.

When the cut-off is next triggered, the previously pressurised sides of the cylinders 20 and 21 are exhausted to the atmosphere and the cycle is repeated in the opposite direction. That is, the knife 80 returns severring the tobacco stream with its other cutting edge and is followed by movement of the carriage 18 which transfers the tobacco portion in chamber 66 to the other side of the measuring tube 12 where it falls through the other aperture 61 into the chute 24. The operation of the cut-off occurs automatically on receipt of a pulse from the control unit 135 or 238.

The portions fall through the chute 24 into the check weigher pan 26 based on a load cell of known construction, in which the deflection of a spring supporting the pan 26 is measured by a linear variable differential transformer, and critically damped by a dashpot containing a viscous fluid. By using a spring of high rate and small deflection which the linear variable differential transformer is able to measure, the natural period of the system can be made very short so that the weighing can be made in less than half a second.

The oscillator 142 supplies an alternating current to one winding of the linear variable differential transformer and the current induced in the other winding is proportional to the movement of the core of the linear variable differential transformer. This induced current is amplified and rectified to provide a signal proportional to weight in the pan 26.

After the weighing, the pan 26 is pivoted by any suitable means (not shown) to discharge the tobacco portion onto the chute or deflector plate 144 which is pivoted on a horizontal axis in and near the centre of its plane. The chute plate is inclined at 60° to the horizontal but can be rotated on its axis by the rotary solenoid 146 to face in either of two directions.

If the resultant weight signal is within preset limits, the tobacco portion in the pan 26 is accepted and the chute or deflector 144 is positioned to discharge the tobacco portion from the pan into a bucket conveyor 29 for transfer to the packing machine (not shown). If the weight signal is outside the limits, the chute or deflector 144 is pivoted to its other position, and the tobacco is directed into the reject hopper 148 for reuse.

If the check weigher 28 is repeatedly registering a light or heavy weight, a signal is fed back to the displacement unit 136 or flow integrator 232 to correct the target totaliser weight. This automatically adjusts the displacement unit 136 or flow integrator 232 to compensate for errors due to, for example a reduction in source strength, or build-up of gum on the measuring tube 12.

The packing machine (not shown) runs at a fixed rate and the nature of the described control of the portion weight is such that dispensing of tobacco portions is irregular and not at fixed intervals. Furthermore, a small percentage of tobacco portions are rejected, so it is necessary to maintain a buffer stock or store of such portions between the dispenser and the packer.

The truck conveyor 152 between novel dispenser and packer (not shown) is of known construction and comprises a number of bucket trucks 29 on a recirculating track. A recirculating chain in an adjacent track drives the trucks by pawls which can be automatically engaged or disengaged from the trucks. The empty trucks 29 are disengaged from the chain and accumulate in a line 155 prior to the filling point. The first truck 29 in the empty truck line 155 is positioned below the chute plate 144 and after filling, it is moved forward to take its place at the end of a line 156 of full trucks 29 with the next empty truck taking its place below the chute plate. The first truck 29 in the full truck line 156 is positioned at a re-engaging point and is re-engaged with the chain as each pawl passes, the next full truck being moved forward to take its place.

The pawls are positioned at regular intervals along the chain which is driven by the packer so that the arrival of the trucks at the packer where they empty their contents is synchronized with the packing operation. The movement of the trucks 29 when disengaged from the chain is by gravity or friction belt.

The length of the line 156 of full trucks 29 is a measure of the buffer stock of weighed portions, and is used to feed back a signal along line 160 to speed up or slow down the feed unit and measuring conveyor. If the line 156 exceeds a preset maximum the feed unit and weigher are switched off, and if the line reduces to zero the packer is switched off.

The circuit shown in FIG. 7 operates as follows:
Radiation from the X-ray tube 118 passes through the tobacco stream and falls on the scintillation counter 121. The absorption of radiation by the tobacco is such that the pulses detected in the scintillator is:

$$N = N_o e^{-mpx}$$

Where
- $N_o$ = count rate without tobacco
- $N$ = count rate with tobacco
- $m$ = mass absorption coefficient
- $p$ = tobacco density
- $x$ = tobacco stream thickness
- $e$ = base of natural logarithm Therefore $mpx = \log_e \frac{N_o}{N}$ As the width $x$ of the tobacco and mass absorption coefficient is constant, the weight/unit length is proportional to $\log N_o - \log N$ or $K - \log N$ assuming that the radiation intensity with no tobacco present is constant.

Radiation pulses from the counter 121 are shaped and amplified and after prescaling feed the log-rate meter 123. The output of the log-rate meter 123 is proportional to log N and is fed to the summer unit 124. The standard radiation count No is also fed to the summer unit, whose output is proportional to log No/N. The continuous pulse train from the analogue-to-digital converter 126 has a frequency which at any instant is a measure of the weight per unit length of the tobacco sample under examination. The frequency proportional to the weight per unit length is multiplied by the length pulses to give a weight of tobacco in the window. This multiplication is carried out by counting and storing the weight per unit length pulses with the counter operating for 0.5 millisecond for each belt length pulse.

Because the radiation gauge window is some distance from the cut-off, a time lag is required between the achievement of the preset total and the actual operation of the knife 80. In the case of the digital system shown in FIG. 7, it is provided by the displacement unit 136 which displaces the operation of the cut-off until a fixed number of oscillations of the oscillator 138 have elapsed since the preset weight was achieved. The fixed number of oscillations corresponding to the distance travelled by the tobacco from the scintillation counter 121 to the cut-off.

In the displacement unit 136, initially all counters are reset and are inhibited from counting. On receiving the first measurement pulse counter 1 starts counting belt pulses. The second measurement pulse enables counter 2 to start counting. Further measurement pulses then cause counters 3, 4, 1, 2, etc., to be selected in sequence.

When using an X-ray source 118 as the source of radiation, to measure tobacco to better than ± 1% allowing for variations within the density of the tobacco a viewing window 120 of 20 thousandths of an inch is selected. The tobacco stream is normally passing the viewing window 120 at a speed of 12 ft/minute, which is equivalent to a 8 millisecond viewing time for a 0.5 oz. tobacco sample. The only source of radiation suitable for this measurement time is an X-ray tube. However, if the viewing window were increased to 200 thousandths of an inch, then other sources could be used.

Although a scintillation counter is diagrammatically shown in FIG. 7, the selection of the radiation detector 121 is dependent upon the measurement time and accuracy required. An ionisation gauge is suitable for viewing times of 20 milliseconds but for viewing times of 8 milliseconds, a scintillation counter is preferred.

Due to the random variation in the emission of radiation from the X-ray tube, it is necessary to have a high count rate to obtain the high measuring accuracy together with a short time constant. A count rate of between 80,000 and 160,000 cps is required.

The scintillation counter is made of adequate size to embrace all the radiation which can pass through the two windows. The choice of counter is between a plastic phosphor and a sodium iodide crystal with a plastic phosphor being essential for count rates in excess of 80,000 cps.

The circuit shown in FIG. 8 operates as follows:

Radiation from the source 218 passes through the tobacco stream and falls on the ionization chamber 224. When a suitable voltage is applied to the electrodes of the ionization chamber a small current is produced which is proportional to the radiation collected by the chamber.

The absorption of radiation by the tobacco is such that the current in the ionization chamber is:

$$I = I_0 e^{-mpx}$$

so:

$$\log_e I/I_0 = mpx$$

and:

$$\log_e I - mpx = \log_e I_0$$

Where $I_0$ is the current without tobacco
$e$ is the base of natural logarithm
$m$ is the mass absorption coefficient
$p$ is the tobacco density
$x$ is the stream thickness The log of the amplified signal from the ionization chamber 224 is then inversely proportional to the weight/unit area of the tobacco. The signal is corrected by the linearizing and inverting circuit 230 to give a signal proportional to weight/unit area.

Since the width of the tube is constant, the signal is also proportional to the weight/unit length of the tobacco stream. (Also, since the cross-section of the tube is constant, the ionization chamber is in effect a density gauge.)

The belt speed signal and corrected amplified ionization chamber signal are multiplied together by the flow integrator 232 to give a continuous analogue signal of flow rate. The flow rate signal is integrated with respect to time by a charged capacity circuit within an integrator 232 until the preset total flow rate is achieved, i.e. ½ oz., 1 oz., or 40 grams at which point the cut-off is triggered and the integrator is restarted.

Because the radiation gauge window 220 is some distance from the cut-off, a time lag is required between the achievement of the preset total and the actual operation of the knife. In the case of the analogue system, shown in FIG. 8, this is provided by a delay timer (not shown) which is automatically adjusted by the tachogenerator output from the belt speed.

The radioisotope source may be Strontium-Yttrium 90, Americium 241, Ruthenium 106, Rhodium 106, or Plutonium 238. The decision as to which radiation source is to be used is determined by the measurement time and accuracy required.

Due to the random variation in the emission of radiation from the radioisotope, it is necessary to have a high source activity to obtain a high measuring accuracy and short time constants. With the geometry required for this application, a source activity in the region of 100 to 1000 millicuries is required.

The cross-section of the measuring tube 12 is typically 1½ × 1½ inches for the ½ oz. and 1 oz. portions, and larger for the 33 to 50 gram portions. The bulk density of the tobacco in the tube is typically 12 lb/ft³ and so a ½ oz. portion is a 2 inch length and 1 oz. portion is a 4 inch length of stream.

The weight per unit length of the tobacco stream has considerable variation and to ensure that the weight of a 2 inch length can be measured accurately, it is necessary that the radiation is confined to a short length of stream and that the time constant of the measurement is correspondingly short.

In practice, the radiation is confined to an approximate 0.2 inch length of stream by making the window in the source shield and/or the opposite side of the stream 0.2 × 1.5 inches, the 0.2 inch dimension line being parallel to the axis of the tube and the 1.5 inch coinciding with the width between the fixed walls of the tube and at right angles to the axis. For the best geometry, it is preferable that the source is a piece of foil of the same dimensions. The ionization chamber is made of adequate size to embrace all the radiation which can pass through the two windows.

Tobacco fed from the feed unit 10 passes into the measuring tube 12 at a rate which may for example be sufficient to yield 60 half oz. portions per minute. In this case, the 0.2 inch length of tobacco through which the radiation passes is replaced in 0.1 seconds, if the measuring tube has a cross-section of 1½ × 1½ inches. The time constant of the measurement should accordingly be less than 0.1 seconds, preferably 0.03 seconds.

In a further alternative embodiment, a duplicate source, gauge and pair of windows is provided with a standard absorption sample to enable correction for reduction in source strength to be made automatically.

Although several embodiments of the invention have been illustrated and described in detail, it is to be expressly understood that the invention is not limited thereto. Various changes in the design and arrangement of parts may be made without departing from the spirit and scope of the invention as the same will now be understood by those skilled in the art.

We claim:

1. A method of dispensing portions of particulate material of predetermined weight, comprising
providing a flow of particulate material through a measuring area,
measuring the flow through the measuring area and providing a signal representing the measured flow rate of the particulate material,
integrating the flow rate signal with respect to time to provide a resultant signal of a value proportional to the total weight of the particulate material passed through the measuring area,
delivering the particulate material to a separating means and separating the particulate material in said separating means from the flow through the measuring area when the value of the resultant signal is proportional to the desired predetermined weight.

2. The method in accordance with claim 1, and measuring the flow through the measuring area by radiation detection.

3. The method in accordance with claim 2, and providing means for integrating to obtain a digital integrated signal.

4. The method in accordance with claim 3, and
obtaining a signal by radiation detection and converting said signal to an analogue signal of a voltage the logarithm of which is inversely proportional to the density of the particulate material in the measuring area,
converting the analogue signal to a series of pulses at a frequency which at any instant is a measure of the density of the particulate material in the measuring area,
opening a gate for a time period proportional to the linear speed of the particulate material through the measuring area and passing the pulses through the gate when open, and
counting the gated pulses and comparing the counted pulses to a preset reference proportional to the desired predetermined weight.

5. The method in accordance with claim 4, and
creating a delay between initiating separation and actual separation of the particulate material in said separating means, the delay being proportional to the linear speed of the particulate material through the measuring area.

6. The method in accordance with claim 5, and
weighing the separated material, and
rejecting such material if not of the desired predetermined weight.

7. The method in accordance with claim 2, and
providing means for integrating to obtain an analogue integrated signal.

8. The method in accordance with claim 7, and
obtaining a signal by radiation detection and amplifying said signal, the logarithm of the amplified signal being inversely proportional to the density of the particulate material in the measuring area,
linearizing and inverting the amplified signal to provide an analogue signal proportional to the density of the particulate material in the measuring area,
multiplying the analogue signal by a signal proportional to the linear speed of the particulate material through the measuring area, and
integrating the multiplied signal.

9. The method in accordance with claim 8, and
creating a delay between initiating separation and actual separation of the particulate material in said separating means, the delay being proportional to the linear speed of the particulate material through the measuring area.

10. The method in accordance with claim 9, and
weighing the separated material, and
rejecting such material if not of the desired predetermined weight.

11. Apparatus for dispensing portions of particulate material of predetermined weight, comprising
tubular means defining a measuring area and causing particulate material to flow therethrough,
means for receiving the flow of particulate material and being operable for separating particulate material from the flow of particulate material through said measuring area,
means including a radiation source and a radiation detector disposed adjacent opposite sides of said measuring area for providing a signal representing the rate of flow of particulate material through said measuring area and for integrating such signal with respect to time thereby providing a signal representing the total weight of the particulate material having passed through said measuring area,
means for providing a reference signal representing the desired predetermined weight, and
means for initiating operation of said separating means when the value of the integrated signal is equal to the value of the reference signal.

12. The apparatus in accordance with claim 11, and
means causing a delay between initiating operation of said separating means and separation of particulate material in said receiving and separating means, the delay being proportional to the linear speed of the flow of particulate material through said measuring area.

13. The apparatus in accordance with claim 12, further comprising
means for weighing said particulate material after separation thereof, and
means for causing the weighed particulate material to be dispensed when of the desired predetermined weight and to be rejected when not of the desired predetermined weight.

14. The apparatus in accordance with claim 13, and
said tubular means being provided with a pair of spaced moving walls each disposed along a different side of said measuring area from the other.

15. The apparatus in accordance with claim 14, and
said tubular means further being provided with two windows each in a side opposite from the other, and
said radiation source and said radiation detector each being disposed adjacent a different one of said windows such that radiation from said source passes into said tubular means through one of said windows, across said measuring area between said moving walls and out through the other of said windows to said detector.

16. The apparatus in accordance with claim 15, and
an adjustable shutter disposed between said radiation source and said window adjacent thereto.

17. The apparatus in accordance with claim 15, and
said radiation source being a source of X-rays.

18. The apparatus in accordance with claim 15, and
said radiation source being a source of Beta Rays.

19. The apparatus in accordance with claim 15, and said radiation source being a source of Gamma Rays.

20. The apparatus in accordance with claim 15, and said radiation detector being a scintillation counter.

21. The apparatus in accordance with claim 15, and said radiation detector being an ionization gauge.

22. The apparatus in accordance with claim 13, and said means for receiving and separating portions of particulate material comprising a carriage disposed at one end of the measuring area and being movable between two terminal positions, said carriage being provided with a pair of chambers each positioned to receive the flow of particulate material from said inspection area when said carriage is in a different one of its terminal positions, and each of said chambers being positioned to discharge a portion of particulate material to said weighing means when the other of said chambers is positioned to receive the flow of particulate material from said measuring area.

23. The apparatus in accordance with claim 22, and said receiving and separating means further comprising a knife disposed between said tubular means and said carriage.

24. The apparatus in accordance with claim 23, further comprising a conveyor means for receiving dispensed portions of particulate material from said weighing means and for transporting said portions to apparatus to be packed thereby.

25. The apparatus in accordance with claim 24, and said conveyor means comprising a plurality of trucks mounted on a recirculating track, means for moving each empty truck in turn to a position to receive a dispensed portion of particulate material from said weighing means for moving each truck with such a portion in turn at regular intervals to a position for discharging the portion therein to the apparatus for packing, and means for permitting lines of empty trucks and trucks with such portions to remain idle between the receiving and discharging positions.

\* \* \* \* \*